(12) United States Patent
Chuang et al.

(10) Patent No.: US 11,241,157 B2
(45) Date of Patent: Feb. 8, 2022

(54) UPPER GASTROINTESTINAL BLEEDING MONITORING SYSTEM

(71) Applicant: MediVisionTech Co., Ltd, Tainan (TW)

(72) Inventors: Chiao-Hsiung Chuang, Tainan (TW); Chien-Cheng Chen, Tainan (TW); Yi-Ju Chen, Tainan (TW)

(73) Assignee: MediVisionTech Co., Ltd, Tainan (TW)

( * ) Notice: Subject to any disclaimer, the term of this patent is extended or adjusted under 35 U.S.C. 154(b) by 364 days.

(21) Appl. No.: 15/626,738

(22) Filed: Jun. 19, 2017

(65) Prior Publication Data
US 2018/0000358 A1 Jan. 4, 2018

(30) Foreign Application Priority Data
Jun. 29, 2016 (TW) ................................. 105120507

(51) Int. Cl.
*A61B 1/00* (2006.01)
*A61B 1/005* (2006.01)
(Continued)

(52) U.S. Cl.
CPC ...... *A61B 5/02042* (2013.01); *A61B 1/00009* (2013.01); *A61B 1/0057* (2013.01);
(Continued)

(58) Field of Classification Search
CPC ... A61B 1/00009; A61B 1/0057; A61B 1/042; A61B 1/05; A61B 1/2736; A61B 5/0013;
(Continued)

(56) References Cited

U.S. PATENT DOCUMENTS 6,432,046 B1 * 8/2002 Yarush ............... A61B 1/00039
600/109
7,828,730 B2 11/2010 Schostek et al.
(Continued)

FOREIGN PATENT DOCUMENTS

TW I285542 B 8/2007
TW M433182 7/2012

OTHER PUBLICATIONS

T. Ghosh, S. A. Fattah and K. A. Wahid, "Automatic bleeding detection in wireless capsule endoscopy based on RGB pixel intensity ratio," 2014 International Conference on Electrical Engineering and Information & Communication Technology, Dhaka, 2014, pp. 1-4 (Year: 2014).*

(Continued)

*Primary Examiner* — Matthew Kremer
*Assistant Examiner* — Samuel C Kim
(74) *Attorney, Agent, or Firm* — Huan-Yi Lin; Matthew Lee (57) ABSTRACT

An upper gastrointestinal bleeding monitoring system includes a detection device and a signal processing device to determine bleeding condition of an upper gastrointestinal tract by using relation of time and intensity ratios of RGB three primary colors. The detecting device is placed to the upper gastrointestinal tract of a patient via his/her mouth or nasal passage and then stay the upper gastrointestinal tract for several days for detection of bleeding. The signal processing device may receive and display signal from the detection device to help medical professionals check if bleeding occurs in an upper gastrointestinal tract. Moreover, a procedure of determination of bleeding in an upper gastrointestinal tract with the upper gastrointestinal bleeding monitoring system is described.

8 Claims, 7 Drawing Sheets

(51) Int. Cl.
*A61B 1/273* (2006.01)
*A61B 5/00* (2006.01)
*A61B 5/02* (2006.01)
*A61B 5/07* (2006.01)
*A61B 5/103* (2006.01)
*A61B 5/1455* (2006.01)

(52) U.S. Cl.
CPC .......... *A61B 1/2736* (2013.01); *A61B 5/0013* (2013.01); *A61B 5/0084* (2013.01); *A61B 5/073* (2013.01); *A61B 5/1032* (2013.01); *A61B 5/14552* (2013.01); *A61B 5/42* (2013.01); *A61B 5/4216* (2013.01); *A61B 5/6871* (2013.01); *A61B 5/746* (2013.01); *A61B 2560/0214* (2013.01)

(58) Field of Classification Search
CPC . A61B 5/0084; A61B 5/02042; A61B 5/0261; A61B 5/073; A61B 5/103; A61B 5/1032; A61B 5/1034; A61B 5/14552; A61B 5/42; A61B 5/4216; A61B 5/447; A61B 5/6871; A61B 5/746; A61B 2560/0214; G01J 3/46–528; G06K 9/4652; G06T 7/90; G01D 7/005
See application file for complete search history.

(56) References Cited

U.S. PATENT DOCUMENTS

| | | |
|---|---|---|
| 8,005,536 B2 | 8/2011 | Imran |
| 8,790,248 B2 | 7/2014 | Uchiyama et al. |
| 8,911,368 B2 | 12/2014 | Rabinovitz et al. |
| 2006/0189846 A1* | 8/2006 | Huang .................. A61B 1/041 600/160 |
| 2008/0065105 A1* | 3/2008 | Larkin ............... A61B 1/00193 606/130 |
| 2008/0228047 A1* | 9/2008 | Parks ................. A61B 1/00147 600/302 |
| 2009/0018396 A1 | 1/2009 | Takizawa et al. |
| 2009/0076325 A1* | 3/2009 | Yokoi .................... A61B 1/041 600/118 |
| 2009/0253999 A1 | 10/2009 | Aoki et al. |
| 2011/0306855 A1 | 12/2011 | Rabinovitz et al. |
| 2012/0101391 A1 | 4/2012 | Okada et al. |
| 2012/0136209 A1* | 5/2012 | Kostenich ................ A61B 5/42 600/109 |
| 2013/0172672 A1 | 7/2013 | Iddan et al. |
| 2014/0031659 A1* | 1/2014 | Zhao ................. A61B 1/00009 600/371 |
| 2014/0333743 A1* | 11/2014 | Gilreath ............ A61B 1/00009 348/74 |
| 2015/0105614 A1* | 4/2015 | Igarashi ............... A61B 1/0646 600/104 |
| 2015/0141782 A1* | 5/2015 | Adler ................. A61B 1/00009 600/371 |
| 2015/0208958 A1* | 7/2015 | Kaku .................. A61B 1/0638 600/339 |
| 2016/0239965 A1* | 8/2016 | Kuramoto ................ A61B 1/05 |

OTHER PUBLICATIONS

Al-Rahayfeh, A. A., & Abuzneid, A. A. (2010). Detection of Bleeding in Wireless Capsule Endoscopy Images Using Range Ratio Color. The International Journal of Multimedia & Its Applications, 2(2), 1-10. doi:10.5121/ijma.2010.2201 (Year: 2010).*

* cited by examiner

UPPER GASTROINTESTINAL BLEEDING MONITORING SYSTEM

CROSS-REFERENCE TO RELATED APPLICATIONS

This application claims priority to Taiwan Patent Application No. 105120507, filed Jun. 29, 2016, the content of which are hereby incorporated by reference in their entirety.

FIELD OF THE INVENTION

The present invention relates to a method and a monitoring system for medical diagnosis and recognition, particularly relates to a method and an upper gastrointestinal bleeding monitoring system.

BACKGROUND OF THE INVENTION

Using a gastroscopy to view an upper gastrointestinal tract is common. The endoscope help surgeons evaluate various symptoms that include persistent abdominal pain, nausea vomiting, and bleeding. Moreover, the gastroscopy is a very excellent tool for treating the cause of bleeding in the upper gastrointestinal tract. However, after treating the cause of bleeding, re-bleeding could possibly occur in few days later. Depending on the amount of blood loss, re-bleeding could cause shock and even lead to death.

To our knowledge, there is no medical device that can automatically and consistently detect re-bleeding in the upper gastrointestinal tract. The second gastroscopy may be used for checking the re-bleeding condition. But, the second gastroscopy is applied only when re-bleeding is confirmed by fecal occult blood, low blood pressure, or Hematemesis. However, these indirect sings of re-bleeding mean that the re-bleeding has lasted for a while or the blood loss has reached certain amount.

A capsule endoscopy may be used for detecting the re-bleeding in the upper gastrointestinal tract. Although the capsule endoscopy can provide real-time images of the upper gastrointestinal tract, the capsule quickly pass through esophagus, stomach, and duodenum to the lower gastrointestinal tract. Because the monitoring period is short and the device is costly, it is not applied in the re-bleeding detection. The capsule endoscopy, mentioned in Taiwan Patent Nos. 433182 and 285542, and U.S. Pat. No. 8,911,368, has drawbacks, because it cannot stay and monitor re-bleeding in the upper gastrointestinal tract for several days due to power shortage. An optical detection capsule is disclosed by U.S. Pat. No. 7,828,730 and U.S. Patent Publication No. 20110306855 to detect spectrum absorption of body liquid permeating into a detecting optical path, which differs from an analysis on reflection from body liquid. However, such ideas have not been scientifically approved because gastric contents and food intake could significantly influence the detection and analysis. Some capsules described in U.S. Pat. Nos. 8,790,248 and 8,005,536, and U.S. Patent Publication Nos. 20130172672, 20090253999, and 20090018396 do not mention any detection function for bleeding. For optical detection, U.S. Patent Publication No. 20120101391 discloses plaque measurement within vascular wall by detecting plaques of non-blood subjects such as lipid, cholesterol, and leukocyte body aggregation for analysis on invisible absorption spectrum of specific subjects.

SUMMARY OF THE INVENTION

With respect to the issues mentioned above, an upper gastrointestinal bleeding monitoring system is provided herein to determine the bleeding condition of an upper gastrointestinal tract by using relation of time and intensity ratios of RGB three primary colors.

Accordingly, an upper gastrointestinal bleeding monitoring system of the present invention includes a bleeding detecting device and a signal processing device. The bleeding detecting device is placed to the upper gastrointestinal tract of a patient via his/her mouth or nasal passage. Then, the detecting device stays the upper gastrointestinal tract for several days to consistently monitor whether re-bleeding occurs after bleeding control by gastroscopy.

Accordingly, the signal processing device may receive and display signals from the detection device to help medical professionals check if re-bleeding occurs in the upper gastrointestinal tract.

Accordingly, an upper gastrointestinal bleeding monitoring system of the present invention includes a bleeding detecting device and a signal processing device. The bleeding detecting device is placed to the upper gastrointestinal tract of a patient via his/her mouth or nasal passage. Then, the detecting device stays the upper gastrointestinal tract for several days to consistently monitor whether re-bleeding occurs.

Accordingly, the signal processing device may receive and display signals from the detection device to help medical professionals check if re-bleeding occurs in the upper gastrointestinal tract.

Additionally, the upper gastrointestinal bleeding monitoring system will alarm if the signal analysis considers that re-bleeding occurs.

According to above description, the present invention provides an upper gastrointestinal bleeding monitoring system. The system includes a detection device that includes a cable, a bleeding detecting device, and a signal transmission module, in which the bleeding detecting device is coupled to the signal transmission module with the cable and provided to generate a time signal of RGB three primary colors. The system also includes a signal processing device that receives the time signal of RGB three primary colors from the bleeding detecting device. The signal processing device analyzes an intensity ratio of the time signal of RGB three primary colors, determines the bleeding condition according to the intensity ratio of the time signal of RGB three primary colors, provides bleeding alarm, and evaluates bleeding time.

DETAILED DESCRIPTION OF THE PREFERRED EMBODIMENT

Components and achievement of an upper gastrointestinal bleeding monitoring system according to the present invention may be illustrated in following drawings and embodiments. However, sizes and shape shown on drawings for the upper gastrointestinal bleeding monitoring system do not limit the features of the present invention. In addition, an upper gastrointestinal tract in the present invention includes any organ between esophagus and duodenum.

Figure 1A:
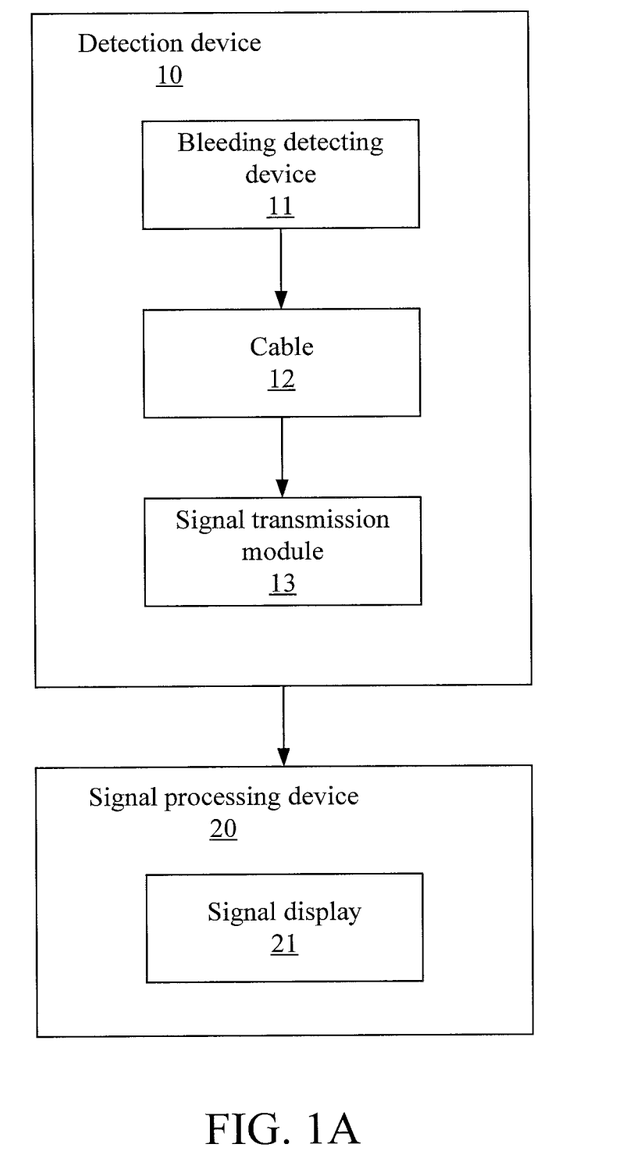
FIG. 1A is a schematic block diagram illustrating an upper gastrointestinal bleeding monitoring system according to the present invention.

FIG. 1A is a schematic block diagram illustrating an upper gastrointestinal bleeding monitoring system according to the present invention. Please refer to FIG. 1A, an upper gastrointestinal bleeding monitoring system of the present invention is provided with a detection device 10 and a signal processing device 20. The detection device 10 includes a bleeding detecting device 11, a signal transmission module 13 and a cable 12. The bleeding detecting device 11 is coupled to the signal transmission module 13 with the cable 12 so as to connect signal acquired from the bleeding detecting device 11 to the signal processing device 20. Furthermore, the bleeding detecting device 11 of the present invention may be equipped with a lighting device, an image lens or a light sensor, and the signal processing device 20 further include a signal display 21.

The light sensor mentioned above maybe provided to detect light intensities in specific frequencies, especially the RGB three primary colors. Shown in FIG. 3, an image capturing apparatus captures RGB images to form color intensity signals. These color intensity signals of RGB three primary colors are displayed on the signal display 21 after processed by the signal processing device 20.

Figure 2:
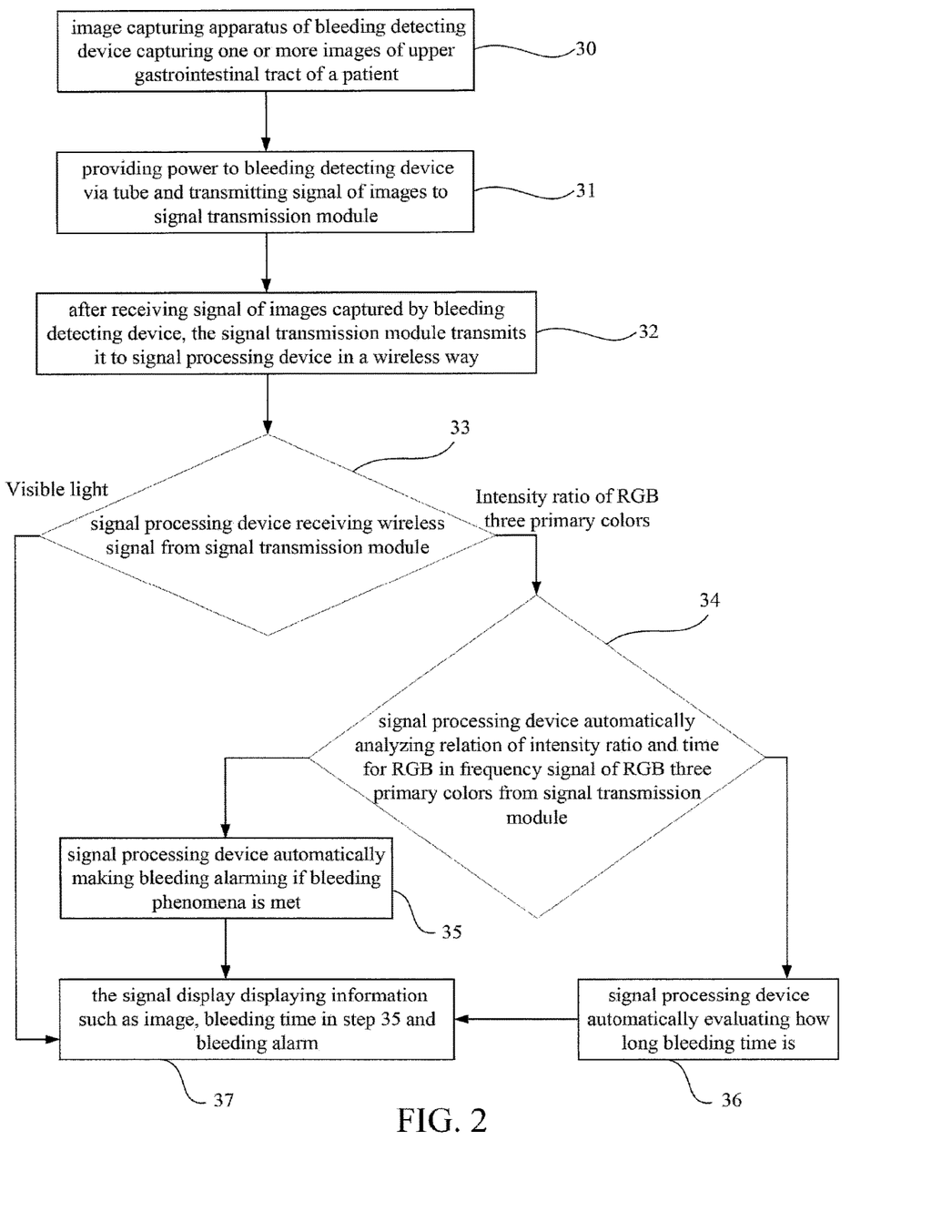
FIG. 2 is a schematic flow chart illustrating steps for an upper gastrointestinal bleeding monitoring system of first embodiment according to the present invention.

FIG. 2 is a schematic flow chart illustrating steps for an upper gastrointestinal bleeding monitoring system according to the present invention, which recites the steps of acquiring the time signal of RGB three primary colors by the bleeding detecting device 11, processing the time signal of RGB three primary colors by the signal processing device 20 and displaying the time signal of RGB three primary colors by the signal display 21.

Accordingly, operating steps for the upper gastrointestinal bleeding are shown in FIG. 2. The steps include:

Step 30: the image capturing apparatus of the bleeding detecting device 11 captures one or more images of an upper gastrointestinal tract of a patient and detects the time signal of RGB three primary colors.

Step 31: the bleeding detecting device 11 is provided with electrical power via the cable 12 and the signal of the images is transmitted to the signal transmission module 13 via the cable 12.

Step 32: the signal transmission module 13 receives the signal of the images captured by the bleeding detecting device 11 and then transmits it to the signal processing device 20 in a wireless way. The bleeding detecting device 11 may include the image capturing apparatus or/and the light sensor.

Step 33: the signal processing device 20 may receive the wireless signal from the signal transmission module 13 and determine whether it is the image signal or the time signal of RGB three primary colors.

Step 34: provided that the wireless signal is determined to be the time signal of RGB three primary colors from the light sensor, the signal processing device 20 automatically analyzes a relation of intensity ratio and time in the time signal of RGB three primary colors from the signal transmission module 13.

Step 35: after analyzing the relation of intensity ratio and time in the time signal of RGB three primary colors in step 34, the signal processing device 20 may compare intensity ratios in the time signal of RGB three primary colors with a disease condition datasheet. Furthermore, bleeding alarm of step 37 is simultaneously and automatically executed if the bleeding threshold is met based on a comparison result.

Step 36: after analyzing the relation of intensity ratio and time in the time signal of RGB three primary colors in step 34, the signal processing device 20 may automatically evaluate how long bleeding time is and display analysis information in step 37.

Step 37: the signal display 21 displays information such as the image signals in step 33, the bleeding time in step 35 and the bleeding alarm in step 36.

The steps mentioned above may be executed with one or more corresponding modules or devices. For example, Step 30 may be executed by the bleeding detecting device 11 of the detection device 10; Step 31 may be executed with the cable 12 of the detection device 10; Step 32 may be executed by the signal transmission module 13 of the detection device 10; Steps 33, 34, 35, 36, and 37 may be executed by the signal processing device 20; and Step 37 may be executed by the signal display 21 of the signal processing device 20.

Details in Step 33 include separating the image signals of the image capturing apparatus from the time signal of RGB three primary colors of the light sensor and processing them separately. On condition that the wireless signal is determined to be the image signal from the bleeding detecting device 11, then Step 37 will be executed to display the image on the signal display 21. On condition that the wireless signal is determined to be the time signal of RGB three primary colors from the bleeding detecting device 11, then Step 34 will be executed to convert the time signal of RGB three primary colors into the intensity ratios for analysis, and Step 35 may be executed to determine whether the bleeding occurs by utilizing light intensities ratios of Table 1 or other databases. If the bleeding phenomenon is determined, making the bleeding alarm in Step 37 will be executed. Besides, the bleeding time may be calculated out in Step 36 and displayed in Step 37 by analyzing the relation of the intensity ratio and the time in the time signal of RGB three primary colors.

Figure 2A:
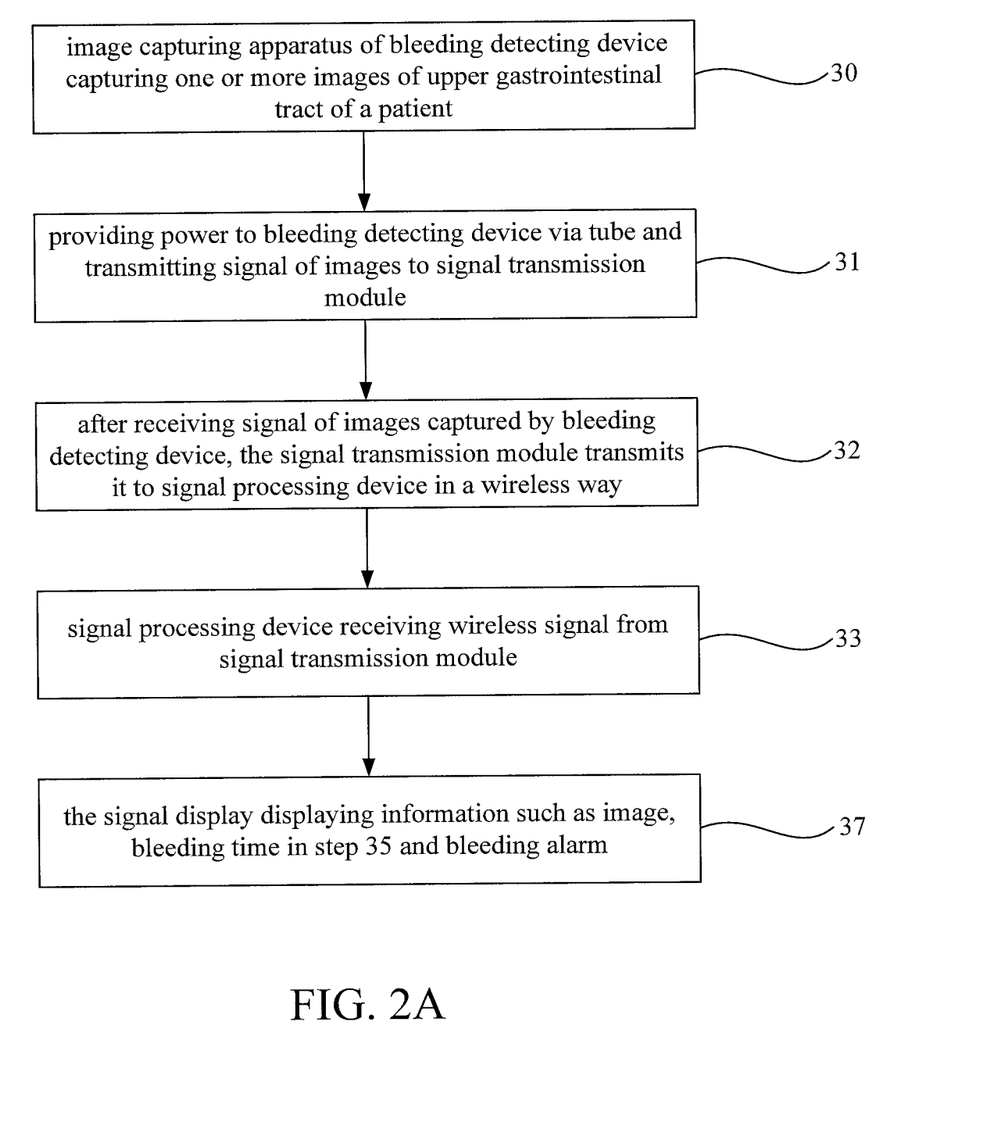
FIG. 2A is a schematic flow chart illustrating steps of displaying image for an upper gastrointestinal bleeding monitoring system of the first embodiment according to the present invention.
Figure 2B:
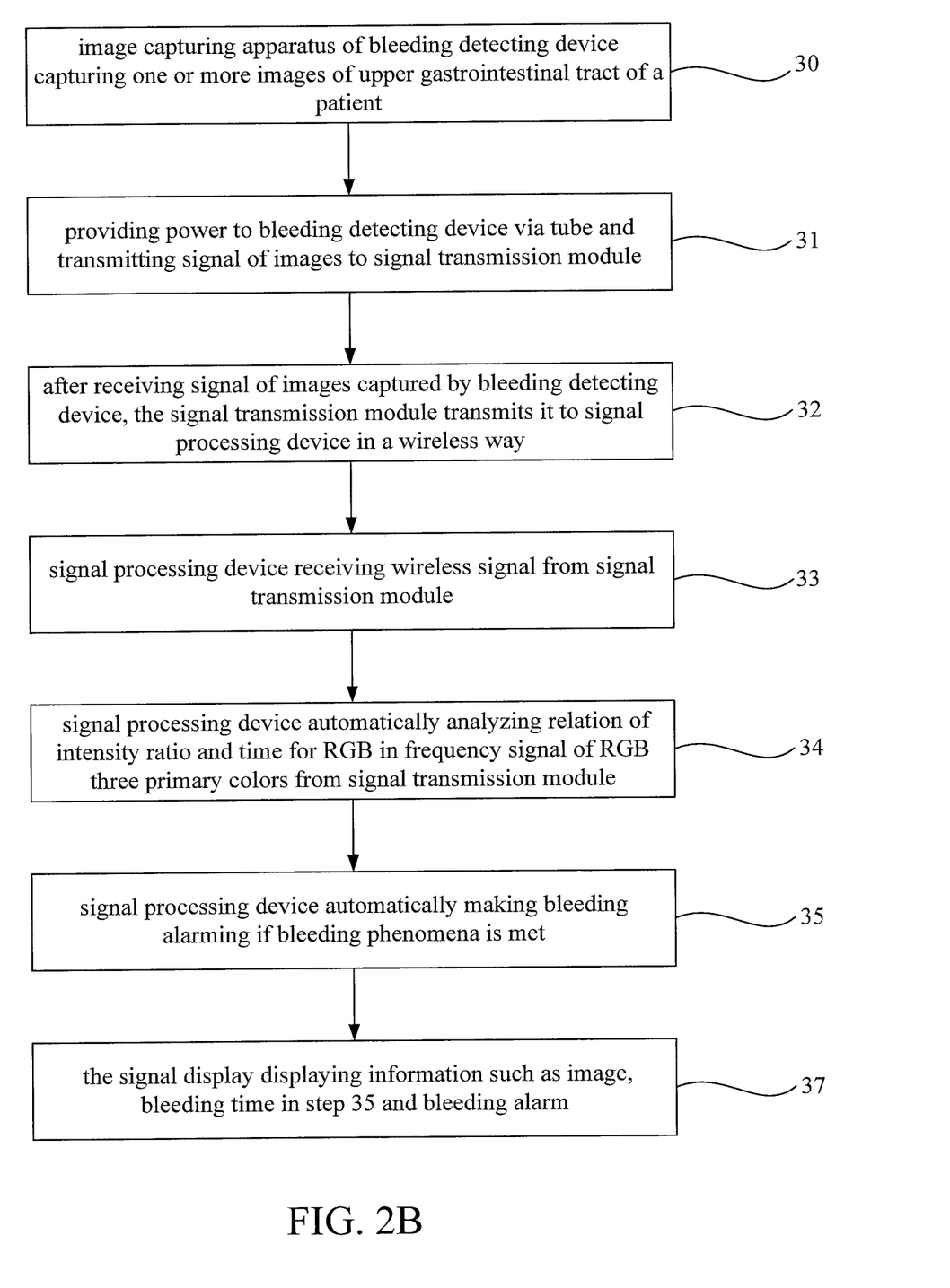
FIG. 2B is a schematic flow chart illustrating steps of making alarm for an upper gastrointestinal bleeding monitoring system of the second embodiment according to the present invention.
Figure 2C:
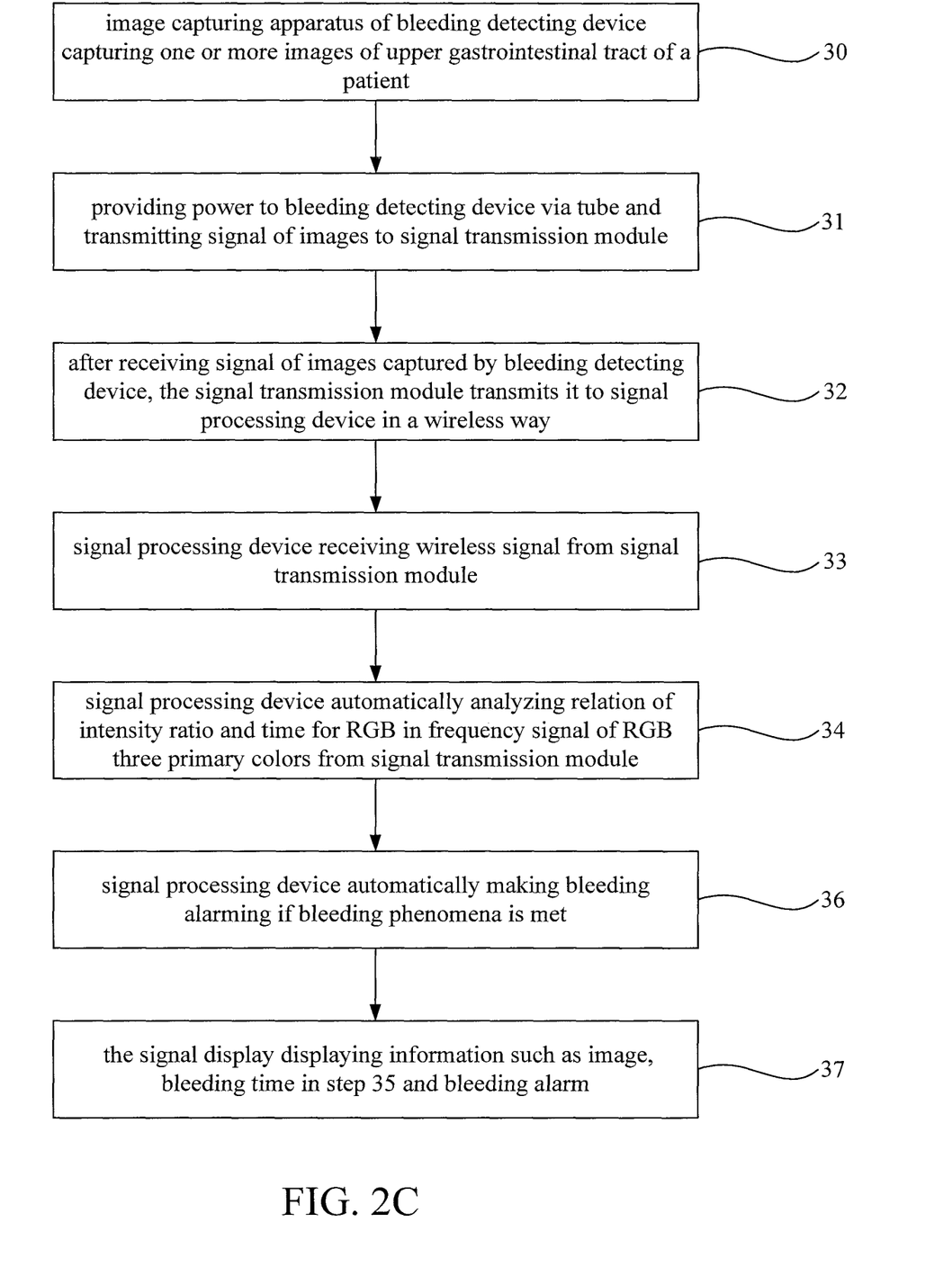
FIG. 2C is a schematic flow chart illustrating steps of evaluating bleeding time for an upper gastrointestinal bleeding monitoring system of the third embodiment according to the present invention.

Accordingly, the steps shown in FIG. 2 may be illustrated by detailed embodiments shown in FIG. 2A, FIG. 2B and FIG. 2C. The first embodiment of FIG. 2A represents the steps of displaying the images with the upper gastrointestinal bleeding monitoring system; the second embodiment of FIG. 2B represents the steps of making bleeding alarm by the upper gastrointestinal bleeding monitoring system; and the third embodiment of FIG. 2C represents the steps of evaluating bleeding time with the upper gastrointestinal bleeding monitoring system.

The first embodiment of displaying the images with the upper gastrointestinal bleeding monitoring system in FIG. 2A is achieved with steps 30, 31, 32, 33, and 37. The image capturing device of the bleeding detecting device 11 is put into the upper gastrointestinal tract of a patient 1 by passing through his/her nasal passage or month with the cable 12 of the detection device 10 and then transmits the signals of the captured image of the upper gastrointestinal tract of the patient 1 to the signal processing device 20 in the wireless way via the signal transmission module 13 (Steps 30, 31, and 32). When the signal processing device 20 judges that the image signal is received (step 33), the image signal from the signal transmission module 13 is automatically displayed by the signal display 21 to show the interior images of the upper gastrointestinal tract for medical professionals (Step 37).

FIG. 2B is a schematic flow chart illustrating steps of making alarm for an upper gastrointestinal bleeding monitoring system of the second embodiment that is implemented by Steps 30, 31, 32, 33, 34, 35 and 37. The image capturing device of the bleeding detecting device 11 is put into the upper gastrointestinal tract of the patient 1 by passing through his/her nasal passage or mouth with the cable 12 of the detection device 10 and then transmits the time signal of RGB three primary colors of the upper gastrointestinal tract of the patient 1 to the signal processing device 20 in the wireless way via the signal transmission module 13 (Steps 30, 31 and 32). Next, on condition that the wireless signal is determined to be the time signal of RGB three primary colors by the signal processing device 20 (Step 33), the time signal of RGB three primary colors from the signal transmission module 13 is simultaneously and automatically converted into the relation of intensity ratios of RGB three primary colors by the signal processing device 20 during health care or monitoring (Step 34). If the relation of intensity ratios of RGB three primary colors is determined to be a bleeding condition in reference to the disease condition datasheet (Step 35) or other database, the bleeding condition may be real-time displayed by the signal display 21 and alarm (Step 37).

FIG. 2C is a schematic flow chart illustrating steps of evaluating bleeding time for the upper gastrointestinal bleeding monitoring system of the third embodiment that is implemented by Steps 30, 31, 32, 33, 34, 36 and 37. The image capturing device of the bleeding detecting device 11 is put into the upper gastrointestinal tract of the patient 1 by passing through his/her nasal passage or mouth with the cable 12 of the detection device 10 and then transmits the time signal of RGB three primary colors of the upper gastrointestinal tract of the patient 1 to the signal processing device 20 in the wireless way via the signal transmission module 13 (Steps 30, 31 and 32). On condition that the wireless signal is determined to be the time signal of RGB three primary colors by the signal processing device 20 (Step 33), the time signal of RGB three primary colors from the signal transmission module 13 is simultaneously and automatically converted into the relation of intensity ratios of RGB three primary colors by the signal processing device 20 (Step 34). The signal processing device 20 evaluates bleeding time by acquiring physiological condition and time according to the relation of intensity ratios of RGB three primary colors in reference to the disease condition datasheet (Step 36) or other database, and the bleeding time may be real-time displayed by the signal display 21 for the medical professionals (Step 37).

TABLE 1

| Physiological condition of upper gastrointestinal tract | Red(R)/Green(G) |
|---|---|
| Bubble liquid | 1.1 |
| Water | 1.2 |
| Empty stomach | 1.5 |
| Deoxygenated blood | 2.1 |
| Oxygenated blood | 2.4 |

TABLE 2

| Physiological condition of upper gastrointestinal tract | Red(R)/Blue(B) |
|---|---|
| Deoxygenated blood | 2.5 |
| Oxygenated blood | 1.3 |

Table 1 and table 2 are examples for the relation of intensity ratios. The values in the disease condition datasheet may be different among different patients. The data in table 1 represents red color intensity divided by green color intensity. The data in table 2 represents red color intensity divided by blue color intensity. On one hand, in reference to table 1, ratio of red and green intensities (R/G) higher than 2 represents a measured color with red tone and bleeding phenomena possibly happens, thus the ratio of red and green intensities is regarded as a major parameter. On the other hand, ratio of red and blue intensities (R/B) is for auxiliary reference and used to distinguish deoxygenated blood and oxygenated blood. Accordingly, the intensity ratio of RGB three primary colors measured by the bleeding detecting device 11 is automatically interpreted whether bleeding happens (Step 36). If ratio of red and green intensities (R/G) for oxygenated blood is close to 2.1, the bleeding alarm will be shown by the signal display 21 (Step 37). In this case, in reference to table 2, a ratio of red and blue intensities (R/B) is further determined to be deoxygenated blood or oxygenated blood. If the ratio of red and blue intensities (R/B) is close to 2.5, a sign of deoxygenated blood is determined, or near 1.3 to be determined to a sign of oxygenated blood and so on.

Figure 3:
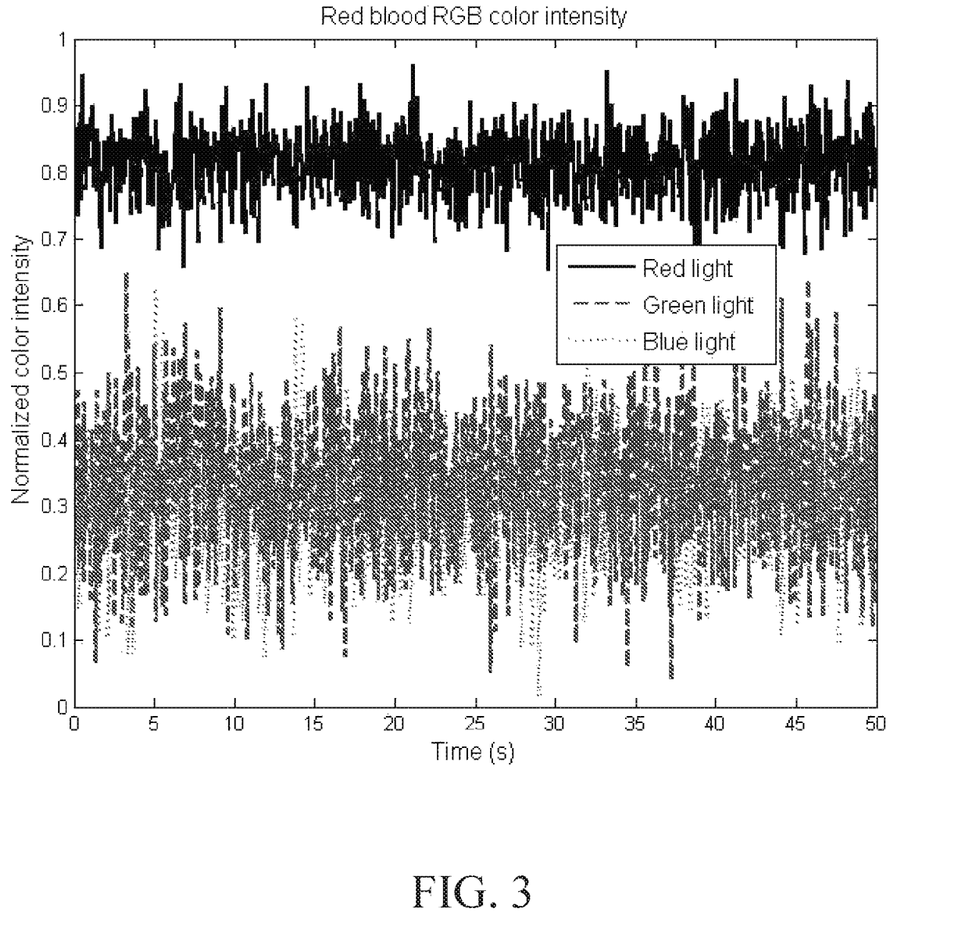
FIG. 3 is a schematic diagram illustrating relation of time signal of RGB three primary colors and time for oxygenated blood according to the present invention.

Furthermore, FIG. 3 is a schematic diagram illustrating relation of time signal of three primary colors and time for oxygenated blood according to the present invention. Please refer to FIG. 3, dark gray lines represent green intensities; light gray lines are blue intensities; and black lines are red intensities. For example, in reference to FIG. 3, red intensities are higher that both of green and blue intensities. Accordingly, the relation of the time signal of RGB three primary colors is converted with the ratios of intensities to show the bleeding condition of oxygenated blood in the upper gastrointestinal tract in reference to the disease condition datasheet. Finally, the period of upper gastrointestinal bleeding may be evaluated with trend analysis such as time statistics (Step 37).

Figure 1B:
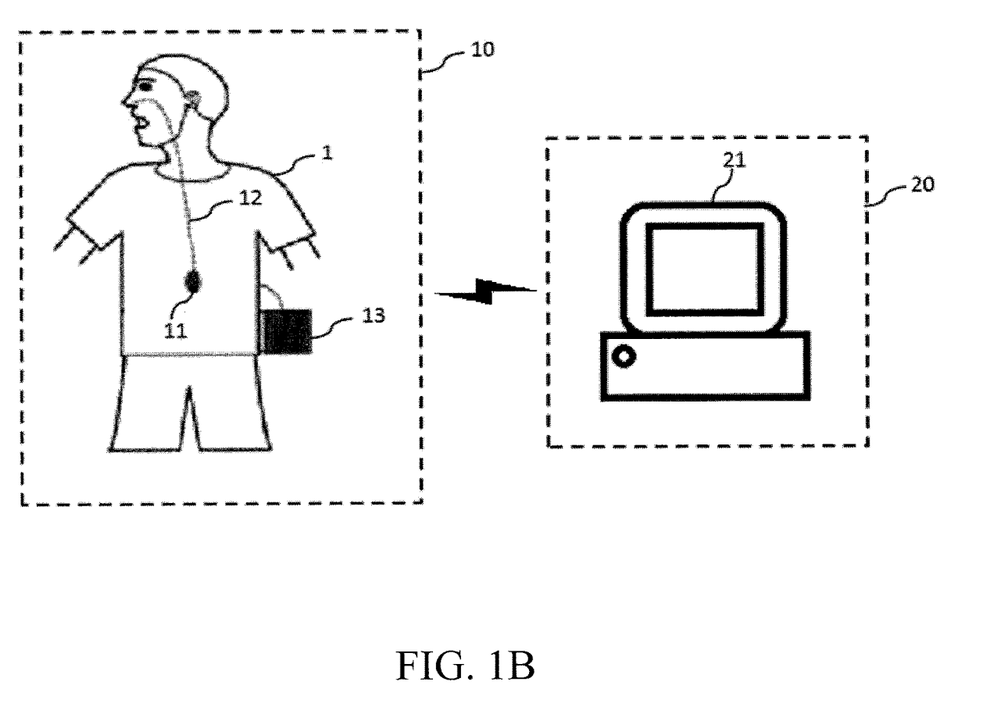
FIG. 1B is a schematic diagram illustrating an upper gastrointestinal bleeding monitoring system of first embodiment according to the present invention.

According to the examples mentioned above, for the operation of the detection device 10, the bleeding detecting device 11 is put into the upper gastrointestinal tract of a patient 1 by passing through his/her nasal passage or mouth, which may do detection without influence on the patient's appetite and digesting. Alternatively, without limitation, the bleeding detecting device 11 may reach to a duodenum of the patient 1 via his/her nasal passage or mouth. First, the detection device 10 is provided to connect the bleeding detecting device 11 and the signal transmission module 13 to a cable 12 and provide them power via an exterior device, such as the signal transmission module 13 for detection without interruption. Next, under the normal operation of the detection device 10, the bleeding detecting device 11 is put into the upper gastrointestinal tract of the patient 1 by passing through his/her nasal passage or mouth, acquires the images with the image capturing device, and then transmits the signal of the images to the signal transmission module 13 via the cable 12. After receiving the signal of the images captured by the bleeding detecting device 11, the signal transmission module 13 may couple to the signal processing device 20 with the cable 12 or transmit the signal of the images to the signal processing device 20 in the wireless way. After analyzing and processing the wired or wireless signal from the signal transmission module 13, the signal processing device 20 may output the interior images of the upper gastrointestinal tract to the signal display 21 for displaying the captured images to the medical professionals for further diagnosis.

Alternatively, in addition of displaying the images of the upper gastrointestinal tract of the patient 1 measured by an optical sensor, the signal processing device 20 may determine whether bleeding occurs or not, by automatically analyzing the signal form the signal transmission module 13, and alarm if bleeding is determined. The signal transmission module 13 further does bleeding analysis on the intensity ratios of RGB three primary colors, automatically evaluates bleeding time according to the relation of intensity ratios and time, and displays them on the signal display 21. Consequently, with the help of electrical apparatus, real-time interpretation and remote monitoring can be implemented. Thus, inefficient monitoring and frequency of checking physiological bleeding signs can be reduced.

While the invention that has been described is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. An upper gastrointestinal bleeding monitoring system for monitoring bleeding in an upper gastrointestinal tract of a subject based on intensity ratios among three primary colors of red, green and blue, comprising:
    a bleeding detecting device comprising:
        a light sensor configured to detect light intensities in specific frequencies corresponding to the three primary colors; and
        wherein said bleeding detection device is configured to be placed in a fixed position in the upper gastrointestinal tract to measure and output a time signal for each of the three primary colors and image data of the upper gastrointestinal tract; and
    a signal processing device configured to receive the time signals of the three primary colors from the bleeding detecting device, wherein the signal processing device is further configured to determine a bleeding condition and time according to intensity ratios among the time signals of the three primary colors, and wherein a probable bleeding condition is determined when the intensity ratio of red to green is greater than 2, and wherein the signal processing device is configured to determine whether there is a sign of deoxygenated blood or a sign of oxygenated blood based on the intensity ratio of red to blue.

2. The upper gastrointestinal bleeding monitoring system according to claim 1, further comprising a cable coupled to the bleeding detecting device configured to adjust the position of the bleeding detecting device in the upper gastrointestinal tract.

3. The upper gastrointestinal bleeding monitoring system according to claim 2, wherein the cable is further coupled to a power supply or a battery from which electrical power is provided to the bleeding detecting device via the cable.

4. The upper gastrointestinal bleeding monitoring system according to claim 1, wherein the bleeding detecting device is configured to be put into the upper gastrointestinal tract of the subject via the subject's nasal passage or mouth.

5. The upper gastrointestinal bleeding monitoring system according to claim 1, further comprising a signal display and wherein the signal processing device is configured to display the time signals of the three primary colors on the signal display.

6. A method for detecting bleeding in an upper gastrointestinal tract of a subject with an upper gastrointestinal bleeding monitoring system of claim 1, comprising:
    obtaining the time signal for each of the three three primary colors of the upper gastrointestinal tract with the bleeding detecting device;
    calculating the intensity ratios of the time signals to determine the bleeding condition and the time of the upper gastrointestinal tract with the signal processing device;
    executing a bleeding alarm if the intensity ratio between red and green has a value greater than 2, and the sign of deoxygenated blood or oxygenated blood based on the intensity ratio between red and blue is determined; and
    displaying the bleeding condition and the time as a result on a signal display.

7. The monitoring system of claim 1, wherein the signal processing device is further configured to output an alarm signal.

8. The monitoring system of claim 1, further comprising a signal transmission module capable of transmitting the time signals of the three primary colors wirelessly to the signal processing device.

* * * * *